United States Patent [19]

Connor et al.

[11] Patent Number: 5,015,468

[45] Date of Patent: May 14, 1991

[54] MANUFACTURE OF TARTRATE DISUCCINATE/TARTRATE MONOSUCCINATE WITH ENHANCED TDS LEVELS

[75] Inventors: Daniel S. Connor, Cincinnati; Robert E. Stidham, Fairfield, both of Ohio

[73] Assignee: The Procter & Gamble Company, Cincinnati, Ohio

[21] Appl. No.: 543,646

[22] Filed: Jun. 26, 1990

[51] Int. Cl.$^5$ .............................................. A61K 7/24
[52] U.S. Cl. .................................................... 424/55
[58] Field of Search ...................................... 424/55

[56] References Cited

U.S. PATENT DOCUMENTS

| | | | |
|---|---|---|---|
| 4,452,820 | 6/1984 | D'Amelia et al. | 426/3 |
| 4,582,709 | 4/1986 | Peters et al. | 426/74 |
| 4,663,071 | 5/1987 | Bush et al. | 252/174.19 |
| 4,689,167 | 8/1987 | Collins et al. | 252/95 |
| 4,721,580 | 1/1988 | Gosselink | 252/90 |
| 4,877,896 | 10/1989 | Maldonado et al. | 560/14 |
| 4,904,824 | 2/1990 | Horng et al. | 562/583 |
| 4,925,586 | 5/1990 | Baker et al. | 252/90 |
| 4,959,409 | 9/1990 | Heinzman et al. | 525/61 |
| 4,968,451 | 11/1990 | Scheibel et al. | 252/549 |

*Primary Examiner*—Shep K. Rose
*Attorney, Agent, or Firm*—Jerry J. Yetter; Richard C. Witte; Douglas C. Mohl

[57] ABSTRACT

Mixtures of tartrate disuccinate and tartrate monosuccinate enriched in the disuccinate species are prepared by reacting isomerically pure D- or L-tartaric acid with maleic anhydride in the presence of sodium hydroxide and calcium hydroxide.

10 Claims, No Drawings

MANUFACTURE OF TARTRATE DISUCCINATE/TARTRATE MONOSUCCINATE WITH ENHANCED TDS LEVELS

TECHNICAL FIELD

The present invention relates to a process for preparing mixtures of tartrate disuccinate and tartrate monosuccinate which are enriched in the disuccinate species. The resulting compositions are especially useful in oral care compositions.

BACKGROUND OF THE INVENTION

The preparation of tartrate monosuccinate ("TMS") and tartrate disuccinate ("TDS") by the reaction, for example, of DL-tartaric acid and maleate is known to provide reaction products comprising mixtures of TMS/TDS having enhanced levels of TMS. Such materials are known for use as builders in detergent compositions.

Separately, it has now been discovered that TMS and TDS are useful as anticalculus ("anti-tartar") agents in oral care products such as dentifrices, mouthwashes, and the like. However, in such uses it is preferred to have enhanced levels of the TDS species. The present invention provides a means for securing TDS/TMS mixtures having the desired enhanced levels of TDS.

BACKGROUND ART

The original synthetic procedure for TMS/TDS and the use of such material as a detergent builder are reported in U. S. Pat. No. 4,663,071, Bush, Connor, Heinzman and Mackey, issued May 5, 1987.

Various processes relating to asserted improvements in the commercial manufacture of TMS/TDS and "Ether Carboxylates" are disclosed in the following documents: U.S. Pat. No. 4,798,907, to MacBrair, Connor, Kretschmar relates to an improved maturation process for preparing oxydisuccinate; U.S. Pat. No. 4,867,901, to Bosch, issued Sept. 19, 1989, relates to a process for preparing TMS and TDS employing certain pH ranges in a recycle process (see also U.S. Pat. No. 4,904,824). Japanese applications 63-28660 and 1-1930, to Masao Nakano, et al., relate to the preparation of tartrate succinates.

SUMMARY OF THE INVENTION

The present invention encompasses a process for preparing mixtures comprising tartrate disuccinate and tartrate monosuccinate, said mixtures being characterized by an enriched ratio of said tartrate disuccinate to said tartrate monosuccinate, comprising reacting a maleate species with isomerically pure D- or L-tartrate, the maleate species being in excess of the tartrate at a mole ratio of from about 1.8:1 to about 4:1, in the presence of an alkali metal hydroxide and an alkaline earth hydroxide in aqueous media. "Isomerically pure" herein means 80% or, more preferably, 95% or more of a single isomer. In the preferred process herein, the maleate species is maleic anhydride.

The present process typically is one wherein the alkali metal hydroxide is sodium hydroxide and the alkaline earth hydroxide is calcium hydroxide.

In general, the process has two stages. The reaction conditions used in the first stage can vary to some extent according to the needs of the formulator. Typically, the first stage of the reaction of D- or L-tartrate with maleate is carried out at a temperature in the range from about 60° C. to about 85° C. for a period of about 0.5 hours to about 2.0 hours.

Immediately following the first stage, the second stage is carried out. This involves allowing the reaction mixture to mature for a substantial period of time at a maturation temperature substantially below the first stage reaction temperature. Typically, the maturation period, i.e., the reaction time for the second stage, is up to about 10 days (5–10 days is common) and the maturation temperature is on the order of 20° C.–40° C., generally about 30° C. The process also comprises the additional steps of calcium removal and maleate removal. Maleate removal is conveniently achieved by means of acidification and filtration of the sodium maleate precipitate that is formed.

Use of isomerically pure tartrate permits formation of a very concentrated, substantially homogeneous reaction medium of maleate and tartrate in the presence of calcium (and sodium) at much lower temperatures than is possible with DL-tartrate. Low temperature maturation permits formation of high levels of TDS because its formation can favorably compete with its relatively reduced rates of decomposition to TMS, maleate and fumarate. The function of the first stage is to generate the homogeneous reaction medium and the second stage to carry it to high TDS.

The invention also encompasses the "high" TDS:TMS ratio product prepared by the process herein.

All percentage, ratios and proportions herein are by weight, unless otherwise specified.

DETAILED DESCRIPTION OF THE INVENTION

The present invention relates to the manufacture of tartrate monosuccinate (TMS) and tartrate disuccinate (TDS) compounds having the following formulae, respectively:

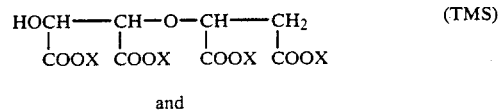

(TMS)

and

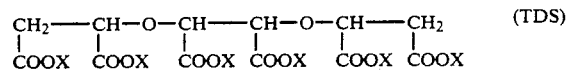

(TDS)

wherein X can be, for example, H or any desired cation, typically alkali metal such as sodium, and the like.

The reaction chemistry herein employs a single tartrate isomer which can be D- or L- and a maleate species, e.g., maleic acid, maleic anhydride (preferred) or the like. Typically, a mole ratio of maleate:tartrate in the range of about 1.8:1 to about 4:1 is used.

The reaction is carried out in aqueous media in the presence of an alkali metal base, e.g., NaOH (preferred) or KOH, and an alkaline earth base, e.g., Ca(OH)$_2$ (preferred) or Mg(OH)$_2$ Typically, the mole ratio of Ca(OH)$_2$:L-tartrate is in the range of about 0.8:1 to about 2.0:1 and the mole ratio of NaOH:L-tartrate is in the range of about 1.9:1 to about 9.4:1. The overall concentration of organic reactants (as Na salts) in the aqueous reaction medium is typically in the range from about 50% to about 75% (wt. basis). Details of typical organic reactant and base concentrations are given in Examples I and II, hereinafter. (Similar mole ratios and concentrations of reactants are employed when the D-tartrate is used in the present process.)

The initial reaction between the tartrate and maleate is carried out at somewhat elevated temperatures of, generally, about 60° C. to about 85° C. for periods, generally, of from about 0.5 hours to about 2 hours. Yields are substantially increased by, thereafter, lowering the temperature to about 30° C. (preferred) for an extended period (3-10 days is typical). Again, reference can be made to the following examples for typical runs.

The following illustrates the process of this invention, but is not intended to be limiting thereof.

EXAMPLE I

The reaction illustrated employs water (122 g.), 50% aq. NaOH (608 g.), L-tartaric acid (150 g.), Ca (OH)$_2$ (118 g.) and maleic anhydride (392 g.).

The water is added to the reaction vessel which is placed in a water bath at 60° C. The NaOH is added with slow stirring. The L-tartaric acid is added slowly and allowed to dissolve. The exotherm is maintained at 60°-80° C. Slowly add the Ca(OH)$_2$ to form a milky suspension. Maleic anhydride is slowly added while keeping the reaction temperature ≦85° C. The mixture is allowed to react at 70°-80° C. for 1 hour during which time it will turn from a chalky white suspension to a honey colored viscous reaction mixture. After 1 hour, the reaction temperature is lowered to 30° C. and maintained for a total reaction duration of 9-10 days. The reaction concentration is maintained at 60% sodium organic salts. The reaction is monitored by HPLC to determine the optimum yield. (Stir the reaction about 0.5 hour before sampling.) When the yield of TMS+TDS approaches a plateau, the reaction is quenched with ca. 1400 g H$_2$O and by removing the calcium.

Calcium removal is as follows. Heat the reaction solution to 70° C. with stirring. Slowly add 161 g Na$_2$CO$_2$ followed by 31.9 g of NaHCO$_3$. Rinse with extra H$_2$O if needed. Stir the mixture at 70° C., pH 10, for 4 hours. After 4 hours, cool to ≦35° C. and filter through coarse fritted filters. Rinse with minimal H$_2$O.

Acid workup is as follows. Add about 450 g of 50% H$_2$SO$_4$ to the "calcium free" solution to pH 4 with stirring to precipitate the residual maleate. Maintain the exotherm at ≦50° C. Let the solution sit overnight to enhance crystallization. Filter through coarse fritted filters via vacuum filter flasks. Use no rinse. Slowly add 160 g of 50% NaOH to the filtrate to pH 9 with stirring. Maintain the exotherm at ≦50° C. Concentrate the solution to about half the current volume (to precipitate Na$_2$SO$_4$) and let sit overnight to enhance crystallization. Filter off the Na$_2$SO$_4$ through coarse fritted filters via vacuum filter flasks. Repeat the evaporation and filtration as often as necessary to remove residual Na$_2$SO$_4$.

Workup in alcohol is as follows. Slowly pour the reaction solution (~40% concentration) into 8.8 L of stirring methanol (MeOH) to removal residual maleate, fumarate, carbonate, and sulfate. The TMS/TDS will precipitate out on the bottom of the vessel as a sticky "gum", while the impurities will remain in the MeOH/H$_2$O layer. Decant/Siphon off as much of the MeOH/H$_2$O as possible and discard. Redissolve the TMS/TDS with 1.6 L H$_2$O using heat and stirring as necessary. Cool to ≦35° C. and repeat with a second extraction. Pour the solution into 6.4 L of stirring MeOH. Again decant/siphon off as much of the MeOH/H$_2$O as possible and discard. Redissolve the TMS/TDS in 1.4 L water and repeat as before, using 5.6 L methanol. Redissolve the TMS/TDS in ca. 1 L H$_2$O. It is now ready for the final workup.

Final workup is as follows. Adjust the reaction solution to about pH 8.5 at 24° C. Heat to ca. 80° C. with stirring and nitrogen sparging to remove residual traces of MeOH. Concentrate the solution to 35% sodium organic salts. Cool to room temperature. Adjust the solution to the desired pH. Add H$_2$O to adjust the final concentration if necessary. Filter through medium fritted filters.

EXAMPLE II

Another, somewhat simpler, procedure which can be employed to prepare TMS/TDS mixtures comprising a higher ratio of TDS to TMS is as follows. The reaction illustrated employs water (86 g.), 50% NaOH (336 g.), L-tartaric acid (150 g.), Ca(OH)$_2$ (89 g.) and maleic anhydride (196 g.).

Add H$_2$O to the reaction vessel which is placed in a water bath at 60° C. Add the NaOH with slow stirring. Slowly add the L-tartaric acid and let dissolve. Maintain the exotherm at 60°-80° C. Slowly add Ca(OH)$_2$ which will form a milky suspension. Slowly add maleic anhydride while keeping the reaction temperature ≦85° C. Allow the mixture to react at 70°-80° C. for 1 hour during which time it will turn from a chalky white suspension to a honey colored viscous reaction mixture. After 1 hour, lower the reaction temperature to 30° C. and maintain it for a total reaction duration of 9-10 days. Maintain the reaction concentration at 60% sodium organic salts. Monitor the reaction by HPLC to determine the optimum yield. (Stir the reaction mixture about 0.5 hour before sampling.) When the yield of TMS+TDS approaches a plateau, proceed by quenching the reaction with ca. 850 g. H$_2$O and by removing the calcium.

Calcium removal is as follows. Heat the reaction solution to 70° C. with stirring. Slowly add 121.9 g. Na$_2$CO$_3$ followed by 24.4 g. NaHCO$_3$ to form a milky suspension. The mole ratio of carbonate to calcium is 1.2 carbonate to 1.0 calcium. Adjust the pH of the suspension to 10.0 at 70° C. with additional Na$_2$CO$_3$ or NaHCO$_3$ if needed. Rinse with extra H$_2$O if needed. Stir the mixture at 70° C., pH 10, for 4 hours. After 4 hours, cool to ≦35° C. and filter through coarse fritted filters. Rinse with minimal H$_2$O.

Workup with methanol is optional. If methanol (MeOH) workup is used, the procedure is the same as in Example I, above.

Final workup is as follows. If a MeOH workup is used, adjust the reaction solution to about pH 8.5 at 24° C. Heat to ca. 80° C. with stirring and nitrogen sparging to remove residual traces of MeOH. Concentrate the solution to 35% sodium organic salts. Cool to room temperature. Adjust the solution to the desired pH. Add H$_2$O to adjust the final concentration if necessary. Filter through medium fritted filters.

The practice of the present invention as illustrated above results in the formation of TDS+TMS mixtures wherein the weight ratio of TDS:TMS is in the range of from about 40:60 to about 60:40.

It is to be understood that the isomerically pure L-tartaric acid used in Examples I and II can be replaced by an equivalent amount of isomerically pure D-tartaric acid, with equivalent results.

The following illustrates the use of compositions prepared in the manner of this invention to prepare oral care compositions.

EXAMPLE III

A toothpaste composition containing the anions from a TDS/TMS mixture is as follows.

| Ingredient | Percent (wt.) |
| --- | --- |
| Water | 14.371 |
| Sorbitol | 24.654 |
| TDS/TMS mixture (per Example I 26% aqueous solution) | 19.233 |
| NaF | 0.243 |
| NaSaccharin | 0.455 |
| Polyethylene Glycol | 2.970 |
| 10 Mol/L NaOH | 0.970 |
| TiO$_2$ | 0.495 |
| FD&C Blue #1 | 0.0495 |
| Silica | 21.780 |
| Glycerin | 8.910 |
| Xanthan Gum | 0.594 |
| Carbopol | 0.198 |
| Flavor | 1.089 |
| Sodium Alkyl Sulfate | 3.960 |

EXAMPLE IV

A mouthwash composition containing the anions from a TDS/TMS mixture is as follows.

| Ingredient | Percent (wt.) |
| --- | --- |
| EtOH (190) | 8.500 |
| Sorbitol (70% aqueous solution) | 18.000 |
| TDS/TMS mixture (per Example II; 25.7% aqueous solution) | 7.800 |
| Polysorbate 80 (Surfactant) | 0.600 |
| Dye (2% aqueous solution) | 0.070 |
| Pluronic F127 (Surfactant) | 0.200 |
| Flavor | 0.075 |
| NaSaccharin | 0.040 |
| Sodium fluoride | 0.050 |
| 50% NaOH | to pH 7 |
| Water qs to | 100.000 |

What is claimed is:

1. A process for preparing anticalculus mixtures comprising tartrate disuccinate and tartrate monosuccinate, said mixtures being characterized by an enriched ratio of said tartrate disuccinate to said tartrate monosuccinate, comprising reacting a maleate species with isomerically pure D- or L-tartrate, the maleate species being in excess over tartrate at a mole ratio of from about 1.8:1 to about 4:1, in the presence of an alkali metal hydroxide and an alkaline earth hydroxide in aqueous media.

2. A process according to claim 1 wherein the maleate species is maleic anhydride.

3. A process according to claim 2 wherein the alkali metal hydroxide is sodium hydroxide and the alkaline earth hydroxide is calcium hydroxide.

4. A process according to claim 2 wherein the reaction of said D- or L-tartaric acid with said maleic anhydride is carried out at a temperature in the range from about 60° C. to about 85° C.

5. A process according to claim 4 wherein the reaction is carried out for a period of about 0.5 hours to about 2.0 hours.

6. A process according to claim 5 wherein, following the reaction, the reaction mixture is allowed to mature for a substantial period of time at a maturation temperature substantially below the reaction temperature.

7. A process according to claim 6 wherein the maturation period of time is up to about 10 days and the maturation temperature is on the order of 20° C.–40° C.

8. A process according to claim 7 which comprises the additional steps of calcium removal and maleate removal.

9. A process acCording to claim 7 in which maleate removal is accomplished by means of acidification and filtration of sodium maleate precipitate.

10. The anticalculus product prepared by the process of claim 7.

* * * * *